(12) United States Patent
Gisolf et al.

(10) Patent No.: US 9,664,665 B2
(45) Date of Patent: May 30, 2017

(54) FLUID COMPOSITION AND RESERVOIR ANALYSIS USING GAS CHROMATOGRAPHY

(71) Applicant: Schlumberger Technology Corporation, Sugar Land, TX (US)

(72) Inventors: Adriaan Gisolf, Houston, TX (US); Youxiang Zuo, Burnaby (CA); Ronald E. G. van Hal, Belmont, MA (US); Jeffrey Crank, Walpole, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 121 days.

(21) Appl. No.: 14/574,351

(22) Filed: Dec. 17, 2014

(65) Prior Publication Data

US 2016/0178599 A1    Jun. 23, 2016

(51) Int. Cl.
| | |
|---|---|
| *G01N 33/28* | (2006.01) |
| *E21B 49/08* | (2006.01) |
| *E21B 49/10* | (2006.01) |
| *G01N 30/88* | (2006.01) |

(52) U.S. Cl.
CPC ....... *G01N 33/2823* (2013.01); *E21B 49/087* (2013.01); *E21B 49/10* (2013.01); *G01N 30/88* (2013.01); *G01N 33/28* (2013.01); *E21B 2049/085* (2013.01); *G01N 2030/8854* (2013.01)

(58) Field of Classification Search
CPC .......... E21B 49/00; E21B 49/08; E21B 49/10; E21B 49/087; G01N 33/2823; G01N 2030/8854; G01N 21/3504
See application file for complete search history.

(56) References Cited

U.S. PATENT DOCUMENTS

| | | | |
|---|---|---|---|
| 4,739,654 | A  | 4/1988  | Pilkington et al. |
| 7,384,453 | B2 | 6/2008  | Bostrom et al. |
| 7,600,413 | B2 | 10/2009 | Shah et al. |
| 7,637,151 | B2 | 12/2009 | Raghuraman et al. |
| 7,654,130 | B2 | 2/2010  | Shah et al. |

(Continued)

OTHER PUBLICATIONS

Totani et al.,"Minami-Aga Oil Feild, Japan, as Viewed from the Crude Oil Properties (Part 3)", Journal of the Japanese Association of Petroleum Technologists, vol. 36, No. 1, Jan. 1971).*

(Continued)

*Primary Examiner* — David A Rogers
(74) *Attorney, Agent, or Firm* — Michael Dae

(57) ABSTRACT

Methods are provided for reservoir analysis. In some embodiments, a reservoir may be analyzed by obtaining abundance ratios at a first measurement station and a second measurement station and determining an abundance ratio trend. Abundance ratios at a third measurement station may be obtained and plotted versus depth with the previously obtained abundance ratios. A change in the abundance ratio trend may be identified and result in further investigation of the reservoir. If the abundance ratio is unchanged, additional abundance ratios may be obtained and plotted versus depth to further evaluate the abundance ratio trend. Methods for reservoir analysis using fluid predictions with and without offset well information are also provided.

6 Claims, 7 Drawing Sheets

(56) References Cited

U.S. PATENT DOCUMENTS

| | | |
|---|---|---|
| 7,658,092 B2 | 2/2010 | Bostrom et al. |
| 7,805,979 B2 | 10/2010 | Reddy et al. |
| 7,822,554 B2 | 10/2010 | Zuo et al. |
| 7,920,970 B2 | 4/2011 | Zuo et al. |
| 7,966,273 B2 | 6/2011 | Hegeman et al. |
| 7,996,154 B2 | 8/2011 | Zuo et al. |
| 8,013,295 B2 | 9/2011 | Zhdaneev et al. |
| 8,028,562 B2 | 10/2011 | Shah et al. |
| 8,250,904 B2 | 8/2012 | Shah et al. |
| 8,271,248 B2 | 9/2012 | Pomerantz et al. |
| 8,512,457 B2 | 8/2013 | Steinecker et al. |
| 8,613,215 B2 | 12/2013 | Lambertus et al. |
| 8,621,912 B2 | 1/2014 | Guieze |
| 8,838,390 B1 * | 9/2014 | Selman ............... E21B 44/00 166/264 |
| 2008/0147326 A1 | 6/2008 | Ellis |
| 2009/0139934 A1 | 6/2009 | Steinecker |
| 2009/0150087 A1 | 6/2009 | Steinecker |
| 2009/0158815 A1 | 6/2009 | Shah et al. |
| 2009/0158820 A1 | 6/2009 | Bostrom et al. |
| 2009/0312997 A1 | 12/2009 | Freed et al. |
| 2010/0018287 A1 * | 1/2010 | Iakimov ............... E21B 47/10 73/23.41 |
| 2010/0127163 A1 | 5/2010 | Zhdaneev et al. |
| 2010/0132450 A1 * | 6/2010 | Pomerantz ....... G01N 33/2823 73/152.28 |
| 2010/0154511 A1 | 6/2010 | Lambertus et al. |
| 2010/0299078 A1 | 11/2010 | Guieze |
| 2011/0011156 A1 | 1/2011 | Guieze |
| 2011/0011157 A1 | 1/2011 | Bourlon et al. |
| 2011/0088895 A1 | 4/2011 | Pop et al. |
| 2012/0021529 A1 | 1/2012 | Nachef et al. |
| 2012/0048108 A1 | 3/2012 | Steinecker et al. |
| 2012/0053838 A1 | 3/2012 | Andrews |
| 2012/0232859 A1 | 9/2012 | Pomerantz et al. |
| 2012/0296617 A1 | 11/2012 | Zuo et al. |
| 2013/0085674 A1 * | 4/2013 | Zhdaneev ............ E21B 49/10 702/6 |
| 2013/0161502 A1 * | 6/2013 | Pomerantz ....... G01N 33/2823 250/255 |
| 2014/0157877 A1 * | 6/2014 | Abad ............... E21B 49/08 73/61.55 |
| 2014/0260586 A1 | 9/2014 | van Hal et al. |
| 2014/0300895 A1 * | 10/2014 | Pope ............... E21B 47/102 356/301 |

OTHER PUBLICATIONS

Duan et al. "Modeling the characterization of the plus fractions by using continuous distribution function," Fluid Phase Equilibria, 345, (2013), pp. 1-10.

Eckert et al. "Effective characterization of petroleum C7+ fractions," Fuel, vol. 102 (2012), pp. 545-553.

Gisolf, et al. "Real Time Integration of Reservoir Modeling and Formation Testing," SPE 121275, prepared for presentation at the 2009 SPE EUROPEC/EAGE Annual Conference and Exhibition held in Amsterdam, The Netherlands, Jun. 8-11, 2009, pp. 1-13.

Hoffmann, et al. "Equilibrium Constants for a Gas-Condensate System," SPE 219-G, Petroleum Transactions, AIME, T.P. 3493, vol. 198, (1953), pp. 1-10.

Hosein et al. "A four coefficient model for extending the heptanes-plus fraction for gas condensate systems," Journal of Petroleum Science and Engineering, 100 (2012), pp. 59-70.

Katz "Overview of Phase Behavior in Oil and Gas Production," SPE 9995, Journal of Petroleum Technology, vol. 35, Jun. 1983, pp. 1205-1214.

Mohamad, et al. "A generalized set of correlations for plus fraction characterization," Pet. Sci., (2012), vol. 9, pp. 370-378.

Rodriguez, et al. "An approach for characterization and lumping of plus fractions of heavy oil," SPE 117446, SPE Reservoir Evaluation & Engineering, Apr. 2010, pp. 283-295.

Whitson "Characterizing Hydrocarbon Plus Fractions," SPE 12233, Society of Petroleum Engineers Journal, vol. 23, Aug. 1983, pp. 683-694.

Zuo, et al. "Integration of Fluid Log Predictions and Downhole Fluid Analysis," SPE 122562, prepared for presentation at the 2009 SPE Asia Pacific Oil and Gas Conference and Exhibition held in Jakarta, Indonesia, Aug. 4-6, 2009, pp. 1-11.

International Search Report and Written Opinion issued in PCT/US2015/057286 on Apr. 15, 2016. 19 pages.

* cited by examiner

FLUID COMPOSITION AND RESERVOIR ANALYSIS USING GAS CHROMATOGRAPHY

BACKGROUND

This disclosure relates to reservoir characterization and fluid analysis and, more particularly, to using downhole gas chromatography to analyze a reservoir.

The composition of a fluid may be determined from various measurements obtained from a fluid downhole in a well. The composition may be used to characterize a reservoir in real-time and adjust drilling strategies. However, composition determinations for a fluid downhole may be difficult and may not provide accurate measurements of all components of a fluid. For example, pumping a fluid to obtain an uncontaminated sample may provide greater accuracy but may be time-consuming, and the acquisition of large numbers of measurements downhole may be expensive. Moreover, extracting a fluid sample to a surface laboratory to provide a detailed composition analysis may result in a greater delay and may be insufficiently responsive for reservoir development, production, and management.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Embodiments of this disclosure relate to various methods for analyzing a reservoir. According to some embodiments, a method for analyzing a reservoir traversed by a wellbore is provided that includes obtaining, from a first measurement station within the wellbore, a first at least one abundance ratio from a first gas chromatogram of a first fluid sample acquired at the first measurement station and obtaining, from a second measurement station within the wellbore, a second at least one abundance ratio from a second gas chromatogram of a second fluid sample acquired at the second measurement station. Additionally, the method includes identifying a trend between the first at least one abundance ratio and the second at least one abundance ratio from the first plot and obtaining, from a third measurement station within the wellbore, a third at least one abundance ratio from a third gas chromatogram of a third fluid sample acquired at the third measurement station. The method further includes determining, using the third at least one abundance ratio, whether a change exists in the abundance ratio trend and using the determination to analyze the reservoir.

According to another embodiment, a method for analyzing a reservoir traversed by a wellbore provided that includes obtaining, from a first measurement station within the wellbore, a first composition of a first fluid sample acquired at the first measurement station and determining an Equation of State (EoS) model for a reservoir fluid using the first composition. The method also includes obtaining, from a second measurement station within the wellbore, a second composition of a second fluid sample acquired at the second measurement station, tuning the EoS model using the second composition, and generating a predicted fluid profile using the EoS model. The method further includes obtaining, from a third measurement station within the wellbore, a component ratio from a gas chromatogram of a third fluid sample acquired at the third measurement station, comparing the component ratio to the predicted fluid profile, and using the comparison to analyze the reservoir.

In another embodiments, a method for analyzing a reservoir traversed by a wellbore is provided that includes obtaining, from at least one offset well, a fluid composition and determining an Equation of State (EoS) model for a reservoir fluid using the fluid composition from the offset well. The method also includes obtaining, from a measurement station within the wellbore, a component ratio from a gas chromatogram of a fluid sample acquired at the station, comparing the component ratio to the predicted fluid profile, and using the comparison to analyze the reservoir.

BRIEF DESCRIPTION OF THE DRAWINGS

Various aspects of this disclosure may be better understood upon reading the following detailed description and upon reference to the drawings in which.

DETAILED DESCRIPTION

Figure 1:
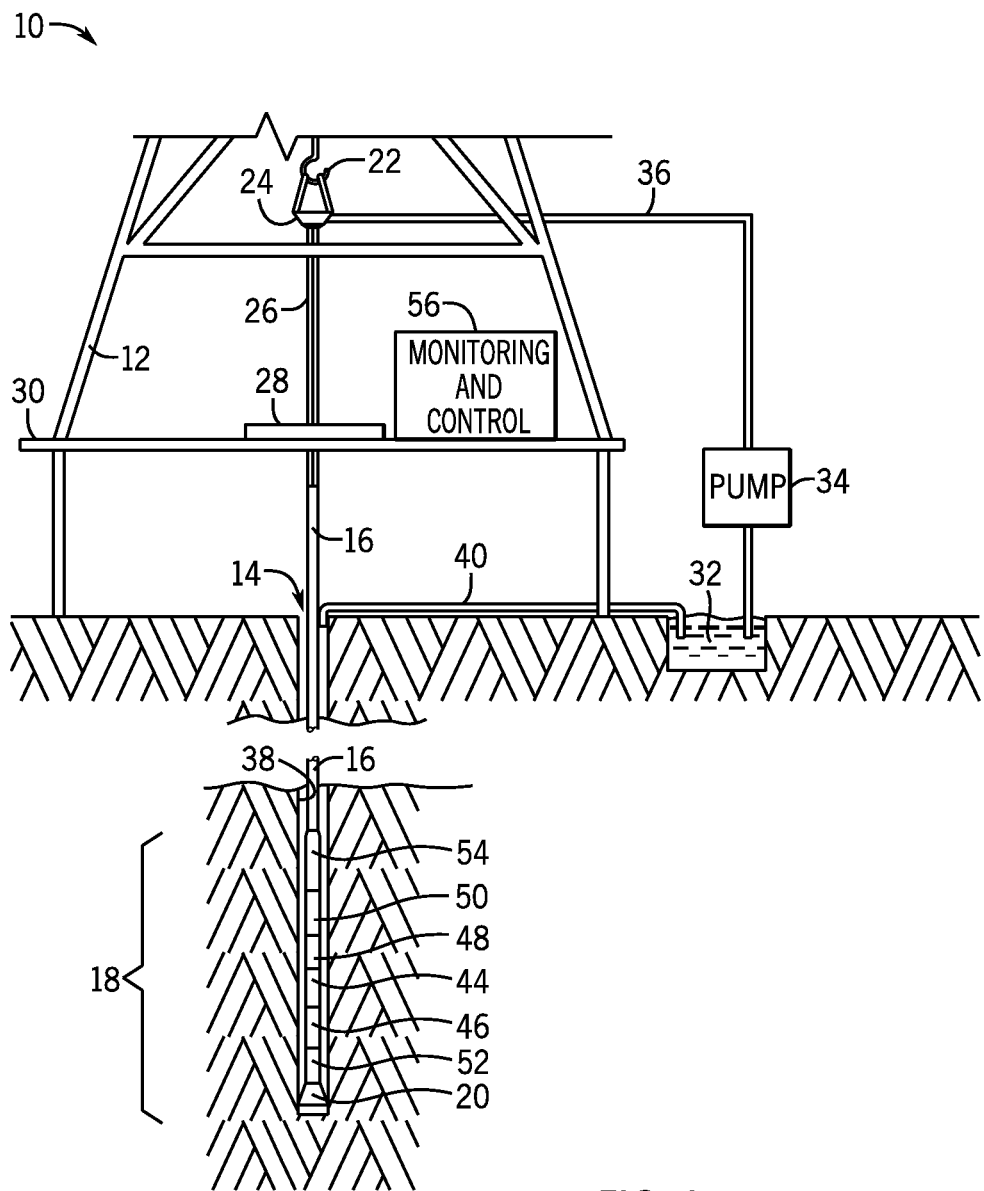
FIG. 1 is a schematic diagram of an example drilling system having a fluid sampling tool in a drill string in accordance with an embodiment of the present disclosure.

Described herein are various embodiments for analyzing a reservoir traversed by a wellbore. In some embodiments, a reservoir may be analyzed by obtaining abundance ratios at a first measurement station and a second measurement station and plotting the abundance ratios versus depth. A trend in abundance ratios may be identified from the plot. Abundance ratios at a third measurement station may be obtained and plotted versus depth with the previously obtained abundance ratios. A change in the abundance ratio trend may be identified and may result in further investigation of the reservoir architecture. If the abundance ratio is unchanged, additional abundance ratios may be obtained and plotted versus depth to further evaluate the abundance ratio trend. In some embodiments, an analyzed fluid sample may be from a heavily contaminated fluid and the analysis may be performed for hydrocarbon fractions unaffected by OBM filtrate contamination, thus enabling a relatively fast fluid analysis and avoiding a cleanup of the fluid.

In some embodiments, a reservoir may be analyzed using fluid predictions without offset well information. In such embodiments, an Equation of State (EoS) model may be built from a fluid composition obtained from a measurement station capable of providing measurements for determination of a fluid composition. A fluid composition from a second measurement station may be obtained and used to tune the EoS model. The EoS model may be used to predict downhole gas chromatography fluid profiles and generate a predicted fluid profile using the assumption that all stations are in the same hydraulic flow unit and the fluid column is in equilibrium. Downhole gas chromatography measurements may be obtained from a target measurement station and compared to the predicted fluid profile. The comparison is evaluated to determine whether the variation between downhole gas chromatography measurements and the predicted fluid profile is acceptable. If the variation is acceptable, the EoS model may be tuned using the downhole GC measurements from the target station and additional downhole GC measurements may be obtained from additional target stations. If the variation is not acceptable, additional fluid compositions may be obtained to determine the source of the variation.

In some embodiments, a reservoir may be analyzed using fluid predictions with offset well information. Data from one or more offset wells may be obtained and used to build an EoS model. The EoS model may be used to predict downhole GC fluid profiles and generate a predicted fluid profile using the assumption that a target well and the offset wells have fluid connectivity and fluid equilibrium. Downhole GC measurements may be obtained from a target measurement station and compared to the predicted fluid profile. The comparison is evaluated to determine whether the variation between downhole GC measurements and the predicted fluid profile is acceptable. If the variation is acceptable, the assumed fluid equilibrium and flow connectivity to the one or more offset wells may be assumed correct. If the variation is not acceptable, additional fluid compositions may be obtained to determine the source of the variation.

These and other embodiments of the disclosure will be described in more detail through reference to the accompanying drawings in the detailed description of the disclosure that follows. This brief introduction, including section titles and corresponding summaries, is provided for the reader's convenience and is not intended to limit the scope of the claims or the proceeding sections. Furthermore, the techniques described above and below may be implemented in a number of ways and in a number of contexts. Several example implementations and contexts are provided with reference to the following figures, as described below in more detail. However, the following implementations and contexts are but a few of many.

More specifically, a drilling system 10 is depicted in FIG. 1 in accordance with one embodiment. While certain elements of the drilling system 10 are depicted in this figure and generally discussed below, it will be appreciated that the drilling system 10 may include other components in addition to, or in place of, those presently illustrated and discussed. As depicted, the system 10 can include a drilling rig 12 positioned over a well 14. Although depicted as an onshore drilling system 10, it is noted that the drilling system could instead be an offshore drilling system. The drilling rig 12 can support a drill string 16 that includes a bottomhole assembly 18 having a drill bit 20. The drilling rig 12 can rotate the drill string 16 (and its drill bit 20) to drill the well 14.

The drill string 16 can be suspended within the well 14 from a hook 22 of the drilling rig 12 via a swivel 24 and a kelly 26. Although not depicted in FIG. 1, the skilled artisan will appreciate that the hook 22 can be connected to a hoisting system used to raise and lower the drill string 16 within the well 14. As one example, such a hoisting system could include a crown block and a drawworks that cooperate to raise and lower a traveling block (to which the hook 22 is connected) via a hoisting line. The kelly 26 can be coupled to the drill string 16, and the swivel 24 can allow the kelly 26 and the drill string 16 to rotate with respect to the hook 22. In the presently illustrated embodiment, a rotary table 28 on a drill floor 30 of the drilling rig 12 can be constructed to grip and turn the kelly 26 to drive rotation of the drill string 16 to drill the well 14. In other embodiments, however, a top drive system could instead be used to drive rotation of the drill string 16.

During operation, drill cuttings or other debris may collect near the bottom of the well 14. Drilling fluid 32, also referred to as drilling mud, can be circulated through the well 14 to remove this debris. The drilling fluid 32 may also clean and cool the drill bit 20 and provide positive pressure within the well 14 to inhibit formation fluids from entering the wellbore. In FIG. 1, the drilling fluid 32 can be circulated through the well 14 by a pump 34. The drilling fluid 32 can be pumped from a mud pit (or some other reservoir, such as a mud tank) into the drill string 16 through a supply conduit 36, the swivel 24, and the kelly 26. The drilling fluid 32 can exit near the bottom of the drill string 16 (e.g., at the drill bit 20) and can return to the surface through the annulus 38 between the wellbore and the drill string 16. A return conduit 40 can transmit the returning drilling fluid 32 away from the well 14. In some embodiments, the returning drilling fluid 32 can be cleansed (e.g., via one or more shale shakers, desanders, or desilters) and reused in the well 14. The drilling fluid 32 may include an oil-based mud (OBM) that may include synthetic muds, diesel-based muds, or other suitable muds.

In addition to the drill bit 20, the bottomhole assembly 18 can also include various instruments that measure information of interest within the well 14. For example, as depicted in FIG. 1, the bottomhole assembly 18 can include a logging-while-drilling (LWD) module 44 and a measurement-while-drilling (MWD) module 46. Both modules can include sensors, housed in drill collars, that can collect data and enable the creation of measurement logs in real-time during a drilling operation. The modules could also include memory devices for storing the measured data. The LWD module 44 can include sensors that measure various characteristics of the rock and formation fluid properties within the well 14. Data collected by the LWD module 44 could include measurements of gamma rays, resistivity, neutron porosity, formation density, sound waves, optical density, and the like. The MWD module 46 can include sensors that measure various characteristics of the bottomhole assembly 18 and the wellbore, such as orientation (azimuth and inclination) of the drill bit 20, torque, shock and vibration, the weight on the drill bit 20, and downhole temperature and pressure. The data collected by the MWD module 46 can be used to control drilling operations. The bottomhole assembly 18 can also include one or more additional modules 48, which could be LWD modules, MWD modules, or some other modules. It is noted that the bottomhole assembly 18 is modular, and that the positions and presence of particular modules of the assembly could be changed as desired. Further, as discussed in detail below, one or more of the modules 44, 46, and 48 can be or can include a fluid sampling tool configured to obtain a sample of a fluid from a subterranean formation and perform downhole fluid analysis to measure various properties of the sampled fluid. These properties may include an estimated density and/or optical density of the OBM filtrate, the sampled fluid, and other fluids. These and other estimated properties may be determined within or communicated to the LWD module 44, such as for subsequent utilization as input to various control functions and/or data logs.

The bottomhole assembly 18 can also include other modules. As depicted in FIG. 1 by way of example, such other modules can include a power module 50, a steering module 52, and a communication module 54. In one embodiment, the power module 50 can include a generator (such as a turbine) driven by flow of drilling mud through the drill string 16. In other embodiments, the power module 50 could also or instead include other forms of power storage or generation, such as batteries or fuel cells. The steering module 52 may include a rotary-steerable system that facilitates directional drilling of the well 14. The communication module 54 can enable communication of data (e.g., data collected by the LWD module 44 and the MWD module 46) between the bottomhole assembly 18 and the surface. In one embodiment, the communication module 54 can communicate via mud pulse telemetry, in which the communication module 54 uses the drilling fluid 32 in the drill string as a propagation medium for a pressure wave encoding the data to be transmitted.

The drilling system 10 can also include a monitoring and control system 56. The monitoring and control system 56 can include one or more computer systems that enable monitoring and control of various components of the drilling system 10. The monitoring and control system 56 can also receive data from the bottomhole assembly 18 (e.g., data from the LWD module 44, the MWD module 46, and the additional module 48) for processing and for communication to an operator, to name just two examples. While depicted on the drill floor 30 in FIG. 1, it is noted that the monitoring and control system 56 could be positioned elsewhere, and that the system 56 could be a distributed system with elements provided at different places near or remote from the well 14.

Figure 2:
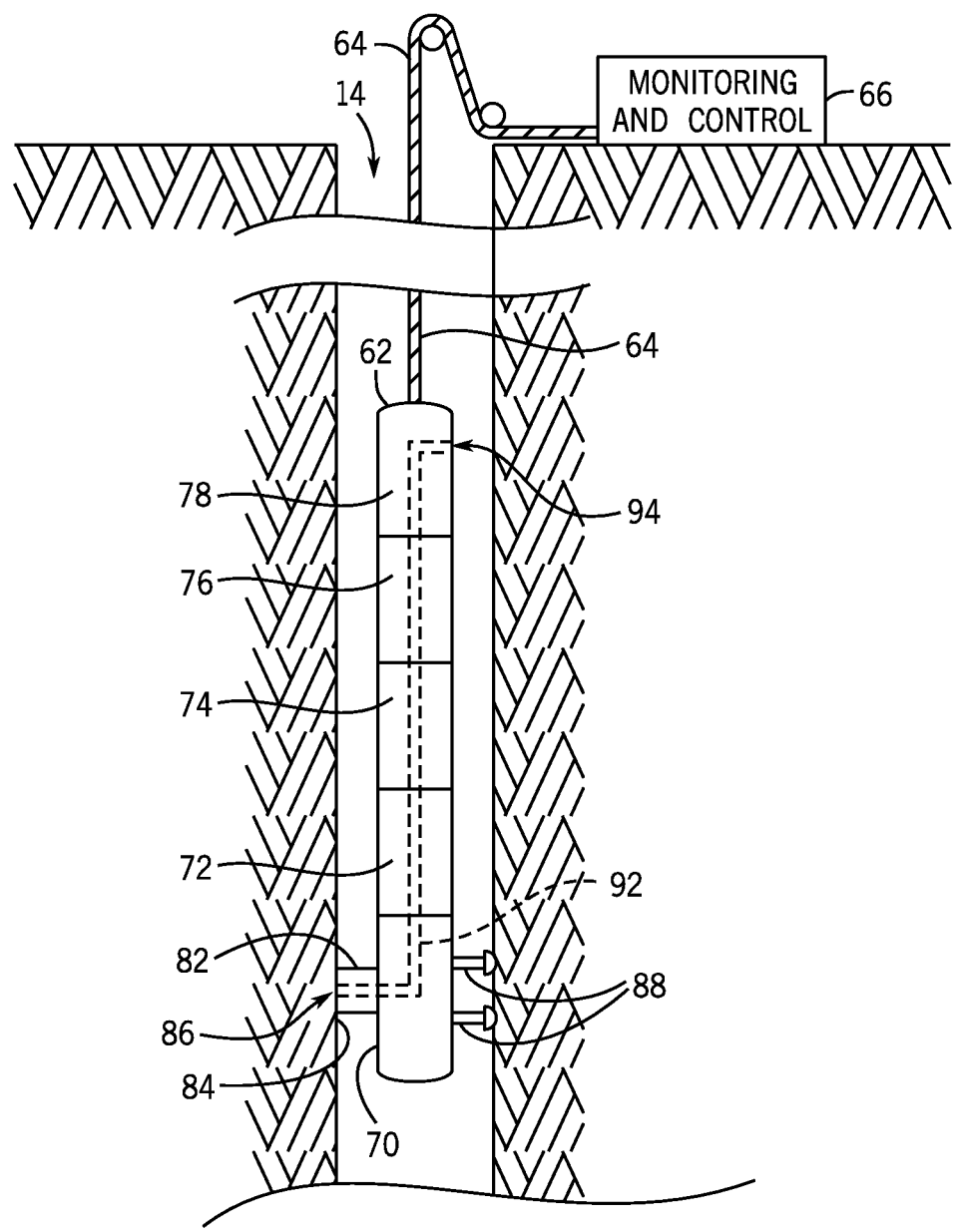
FIG. 2 is a schematic diagram of an example fluid sampling tool deployed within a well on a wireline in accordance with an embodiment of the present disclosure.

Another example of using a downhole tool for formation testing within the well 14 is depicted in FIG. 2. In this embodiment, a fluid sampling tool 62 can be suspended in the well 14 on a cable 64. The cable 64 may be a wireline cable with at least one conductor that enables data transmission between the fluid sampling tool 62 and a monitoring and control system 66. The cable 64 may be raised and lowered within the well 14 in any suitable manner. For instance, the cable 64 can be reeled from a drum in a service truck, which may be a logging truck having the monitoring and control system 66. The monitoring and control system 66 can control movement of the fluid sampling tool 62 within the well 14 and can receive data from the fluid sampling tool 62. In a similar fashion to the monitoring and control system 56 of FIG. 1, the monitoring and control system 66 may include one or more computer systems or devices and may be a distributed computing system. The received data can be stored, communicated to an operator, or processed, for instance. While the fluid sampling tool 62 is here depicted as being deployed by way of a wireline, in some embodiments the fluid sampling tool 62 (or at least its functionality) can be incorporated into or as one or more modules of the bottomhole assembly 18, such as the LWD module 44 or the additional module 48.

The fluid sampling tool 62 can take various forms. While it is depicted in FIG. 2 as having a body including a probe module 70, one or more fluid analysis modules 72, a pump module 74, a power module 76, and a fluid storage module 78, the fluid sampling tool 62 may include different modules in other embodiments. The probe module 70 can include a probe 82 that may be extended (e.g., hydraulically driven) and pressed into engagement against a wall 84 of the well 14 to draw fluid from a formation into the fluid sampling tool 62 through an intake 86. As depicted, the probe module 70 can also include one or more setting pistons 88 that may be extended outwardly to engage the wall 84 and push the end face of the probe 82 against another portion of the wall 84. In some embodiments, the probe 82 can include a sealing element or packer that isolates the intake 86 from the rest of the wellbore. In other embodiments, the fluid sampling tool 62 could include one or more inflatable packers that can be extended from the body of the fluid sampling tool 62 to circumferentially engage the wall 84 and isolate a region of the well 14 near the intake 86 from the rest of the wellbore. In such embodiments, the extendable probe 82 and setting pistons 88 could be omitted and the intake 86 could be provided in the body of the fluid sampling tool 62, such as in the body of a packer module housing an extendable packer.

The pump module 74 can draw the sampled formation fluid into the intake 86, through a flowline 92, and then either out into the wellbore through an outlet 94 or into a storage container (e.g., a bottle within fluid storage module 78) for transport back to the surface when the fluid sampling tool 62 is removed from the well 14. The one or more fluid analysis modules 72, which may also be referred to as a fluid analyzer 72 or a downhole fluid analysis (DFA) module, can include one more modules for measuring properties of the sampled formation fluid, and the power module 76 provides power to electronic components of the fluid sampling tool 62.

In some embodiments, the one or more fluid analysis modules 72 may include an optical analysis module adapted to receive at least a portion of the fluid sample. The optical analysis module may determine an optical property of the fluid sample and to provide an output signal related to or otherwise indicative of the optical property. In such embodiments, the optical analysis module may perform near-infrared optical absorption spectrometry and fluorescence emission measurements for analyzing fluids as they flow through the tool 62. The optical analysis module may be used to determine gas-fraction concentrations and to identify fluid types, respectively.

In some embodiments, the one or more fluids analysis modules 72 of the tool 62 include a gas chromatography (GC) module. The GC module is configured to determine a composition of the fluid sample and to provide an output signal indicative of the determined composition. The GC module may produce what may be referred to as a "gas chromatogram." For the example embodiment using gas chromatography, the gas chromatography module 116 is configured to obtain a chromatogram of sampled formation fluids available within the flowline 92 portion of the tool 62. An example of such a device is described in U.S. Pub. App. No. 2010/0018287, entitled "Wireline Downhole Gas Chromatograph and Downhole Gas Chromatography Method," and U.S. Pat. No. 7,384,453, entitled "Self Contained Chromatography System," each assigned to Schlumberger Technology Corporation and incorporated herein by reference in its entirety. In some embodiments, the GC module may output composition up to C9, e.g., hydrocarbon fractions C1 through C8. In some embodiments, the GC module may output composition up to C30, e.g., hydrocarbon fractions C1 through C29. Additionally, the GC module may also measure N2, CO2, H2S and saturated and aromatic hydrocarbons and abundance ratios. In some embodiments, the GC module of the fluid analysis tool 62 described above may be insensitive to mud filtrate contamination in a sampled fluid by providing analysis of hydrocarbon fractions C1 through C8 (i.e., below C9). Additionally, the GC module of the fluid analysis tool 62 may provide relatively fast profiling of fluid composition ratio changes versus depth. For example, the analysis of hydrocarbon fractions up to C9 may enable analysis of a heavily contaminated fluid without performing a cleanup of the fluid to obtain a less contaminated fluid sample, thus eliminating or reducing cleanup time at the sample location.

In some embodiments, the one or more fluid analysis modules 72 may include a downhole pressure-volume-temperature PVT unit and may obtain microfluidic measurements of the sampled fluid. Embodiments of the tool 62 and fluid analysis modules 72 any include any one of or combination of the modules described above. For example, in some embodiments the tool 62 may include an optical analysis module and a gas chromatography module.

The drilling and wireline environments depicted in FIGS. 1 and 2 are examples of environments in which a fluid sampling tool may be used to facilitate analysis of a downhole fluid. The presently disclosed techniques, however, could be implemented in other environments as well. For instance, the fluid sampling tool 62 may be deployed in other manners, such as by a slickline, coiled tubing, or a pipe string.

Accordingly, the embodiments described above and illustrated in FIGS. 1 and 2 may enable fluid sampling at different depths in the wellbore of the well 14. In some embodiments, systems depicted in FIGS. 1 and 2 may perform multiple fluid measurements by downhole sampling of reservoir fluid at one or more measurement stations (which may include or be referred to as downhole fluid analysis (DFA) stations) within the wellbore, conduct downhole fluid analysis of one or more reservoir fluid samples for each measurement station (including compositional analysis such as estimating concentrations of a plurality of compositional components of a given sample as well as other fluid properties) and, in some embodiments, relate the downhole fluid analysis to an Equation of State (EoS) model of the thermodynamic behavior of the fluid in order to characterize the reservoir fluid at different locations within the reservoir.

Figure 3:
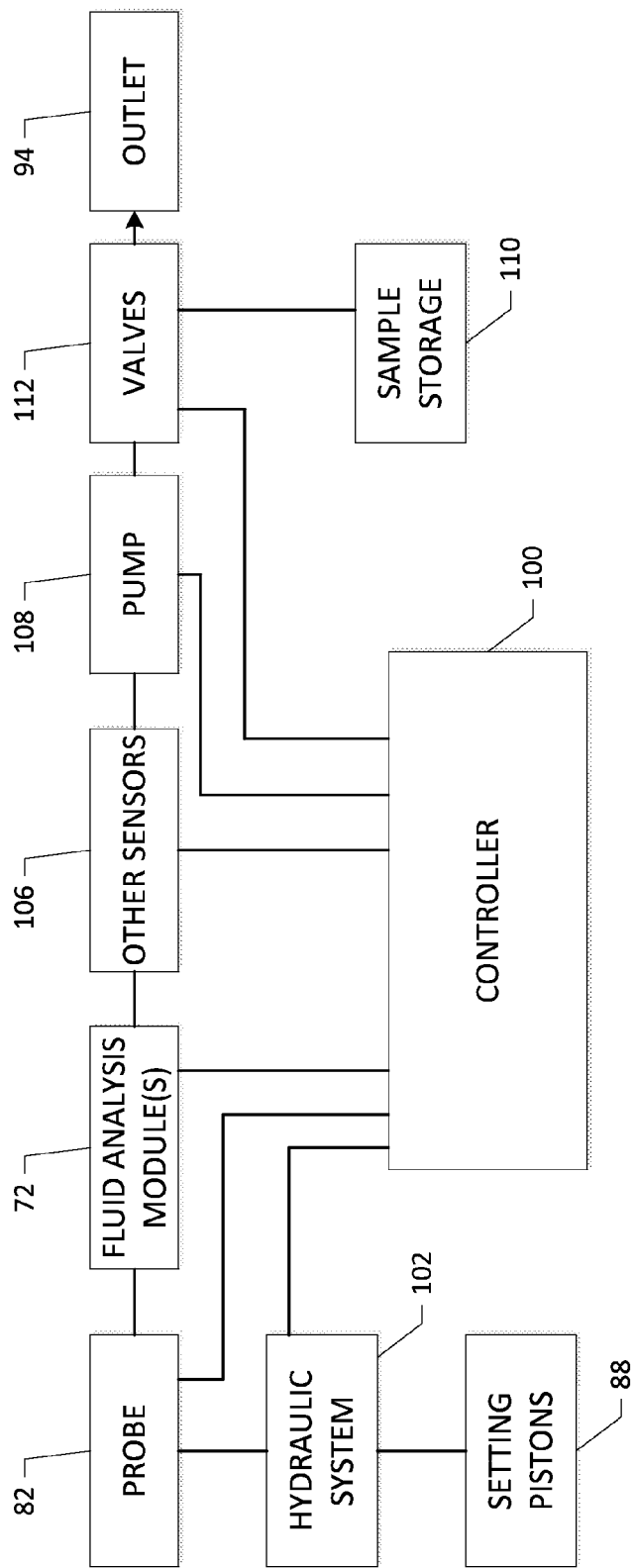
FIG. 3 is a block diagram of components of an example fluid sampling tool operated by a controller in accordance with an embodiment of the present disclosure.

Additional details as to the construction and operation of the fluid sampling tool 62 may be better understood through reference to FIG. 3. As shown in this figure, various components for carrying out functions of the fluid sampling tool 62 can be connected to a controller 100. The various components can include a hydraulic system 102 connected to the probe 82 and the setting pistons 88, the one or more fluid analysis modules 72 discussed above, one or more other sensors 106, a pump 108, and valves 112 for diverting sampled fluid into storage devices 110 rather than venting it through the outlet 94. The controller 100 may include or be coupled to an operator interface (not shown) that provides logs of predicted formation fluid properties that are accessible to an operator.

In operation, the hydraulic system 102 can extend the probe 82 and the setting pistons 88 to facilitate sampling of a formation fluid through the wall 84 of the well 14. It also can retract the probe 82 and the setting pistons 88 to facilitate subsequent movement of the fluid sampling tool 62 within the well. The one or more fluid analysis modules 72 can measure properties of the sampled formation fluid in accordance with the embodiments described above. For example, an optical analysis module may measure optical properties such as optical densities (absorbance) of the sampled formation fluid at different wavelengths of electromagnetic radiation. Using the optical densities, the composition of a sampled fluid (e.g., weight fractions or volume fractions of its constituent components) can be determined. In another example, as described above, a gas chromatography module may determine composition of the fluid sample and provide an output signal indicative of the determined composition. Other sensors 106 can be provided in the fluid sampling tool 62 (e.g., as part of the probe module 70 or the fluid analysis module 72) to take additional measurements related to the sampled fluid. In various embodiments, these additional measurements could include reservoir pressure and temperature, live fluid density, live fluid viscosity, electrical resistivity, saturation pressure, and fluorescence, to name several examples. In some embodiments, as mentioned above, some or all of other sensors 106 may be incorporated into a DFA module (e.g., such as in a PVT unit) of the fluid sampling tool 62.

Any suitable pump 108 may be provided in the pump module 74 to enable formation fluid to be drawn into and pumped through the flowline 92 in the manner discussed above. Storage devices 110 for formation fluid samples can include any suitable vessels (e.g., bottles) for retaining and transporting desired samples within the fluid sampling tool 62 to the surface. Both the storage devices 110 and the valves 112 may be provided as part of the fluid storage module 78.

In the embodiment depicted in FIG. 3, the controller 100 can facilitate operation of the fluid sampling tool 62 by controlling various components. Specifically, the controller 100 can direct operation (e.g., by sending command signals) of the hydraulic system 102 to extend and retract the probe 82 and the setting pistons 88 and of the pump 108 to draw formation fluid samples into and through the fluid sampling tool. The controller 100 can also receive data from the fluid analysis module 72 and the other sensors 106. This data can be stored by the controller 100 or communicated to another system (e.g., the monitoring and control system 56 or 66) for analysis. In some embodiments, the controller 100 is itself capable of analyzing the data it receives from the spectrometer 104 and the other sensors 106. The controller 100 can also operate the valves 112 to divert sampled fluids from the flowline 92 into the storage devices 110.

In some embodiments, geological and other processes may produce systematic or chaotic fluid property variations in, for example, light and heavy oilfields. In such instances, compressible fluids such as light oils and gas condensate may exhibit an increase in the mole fractions of light hydrocarbon fractions with decreasing depth due to oil field charging and gravitational effects. Additionally, fluids may also exhibit changing component abundance ratios with depth. In contrast, processes such as biodegradation can produce relatively complex vertical and lateral compositional and fluid property gradients on a range of reservoir scales.

As described further below, in some embodiments the fluid analysis tool 62 with a GC module may be used to determine changes in, for example, abundance ratios or relative fluid compositions versus depth to analyze a reservoir. For example, in some embodiments, abundance ratios (or relative compositions) of N2, CO2, and hydrocarbon fractions up and including C8 may be plotted against depth to identify changes. In some embodiments, hydrocarbon fractions up to C30 may be plotted against depth to identify changes. The GC module of the fluid analysis tool 62 may enable relatively fast and efficient fluid analysis such that changes verses depth may be plotted in small depth increments to identify subtle changes in fluids.

The processes described below and illustrated in FIGS. 4-6 may be implemented using various data sets obtained from different implementations of the GC module of the fluid analysis tool 62, such as GC measurements up to C9, GC measurements up to C30, or GC measurements above C30. In such instances, although the time to obtain a suitable fluid sample, the time to obtain fluid analysis, and the range of compositional measurements may differ between embodiments of the fluid analysis tool 62 and fluid analysis module 72 the processes for reservoir analysis may be performed as described below and illustrated in FIGS. 4-6. For example, oil-based and synthetic muds may be assumed to contain carbon fractions above C9 (e.g., synthetic muds may contain C12 to C14); consequently, after a small amount of fluid is pumped, the contamination levels of the fluid may be too high for conventional GC analysis or analysis of fractions above C9. Thus, in such embodiments, the abundance ratios up to C9 for a heavily contaminated fluid may be obtained in a relatively short amount of time without the need to perform a full cleanup to obtain a less contaminated fluid sample. The elimination or reduction of cleanup time may enable relatively fast sampling and analysis of the fluid at multiple sample location.

Figure 4:
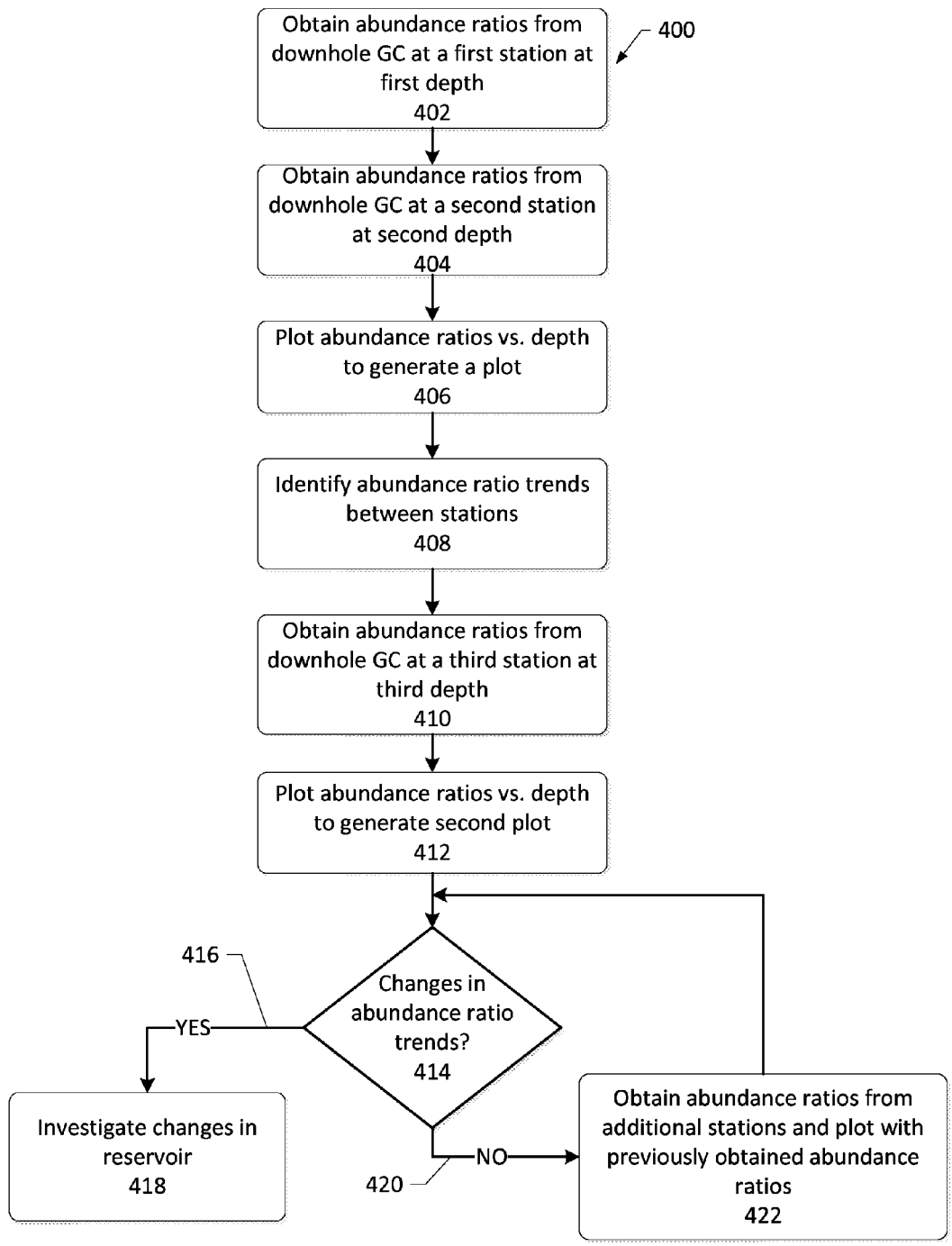
FIG. 4 is a block diagram of an example process for fluid analysis and reservoir characterization using abundance ratio trends in accordance with an embodiment of the disclosure.

FIG. 4 depicts a process 400 for reservoir analysis by plotting abundance ratios vs. depth in accordance with an embodiment of the disclosure. Initially, abundance ratios from a downhole gas chromatogram at a first measurement station at a first depth may be obtained (block 402). As described above, the gas chromatogram may be obtained from a fluid sample acquired at the first measurement station by using the fluid analysis module 72 of the fluid analysis tool 62 described above. As noted above, in some embodiments, the fluid sample analyzed by the fluid analysis module 72 may be from a heavily contaminated fluid and the analysis may be abundance ratios up to C9, thus enabling a relatively fast analysis of the fluid without performing a full cleanup.

As shown in FIG. 4, abundance ratios from a downhole gas chromatogram at a second measurement station at a second depth may also be obtained (block 404). Here again, the gas chromatogram may be obtained from a fluid sample (e.g., in some embodiments from a heavily contaminated fluid) acquired at the second measurement station by using the fluid analysis module 72 of the fluid analysis tool 62 described above. The obtained abundance ratios from the first and second measurement stations may be plotted versus depth (block 406) to produce a first plot. Next, abundance ratios trends between the stations may be identified (block 408). For example, an abundance ratio trend may include an increase in one or more abundance ratios, a decrease in one or more abundance ratios, a linear trend in one or more abundance ratios, a non-linear trend in one or more abundance ratios, or any other suitable trends.

Next, abundance ratios from a downhole gas chromatogram at a third station at a third depth may be obtained (block 410). As described above, the gas chromatogram may be obtained from a fluid sample (e.g., in some embodiments from a heavily contaminated fluid) acquired at the third measurement station by using the fluid analysis module 72 of the fluid analysis tool 62. The third abundance ratio and the previously obtained first and second abundance ratios may be plotted versus depth (block 412) to generate a second plot. The plot may be evaluated to determine changes in abundance ratio trends (decision block 414). For example, in some embodiments the trend may be compared to a threshold to determine if a change occurred in the trend, e.g., any deviation in the trend greater than the threshold may be considered a change in the abundance ratio trend. In other embodiments, suitable statistical techniques may be used to determine whether change occurred in the abundance ratio trend.

If there are changes in the abundance ratio trends (line 416), changes in the reservoir (e.g., changes in reservoir architecture) may then be investigated (block 418). For example, additional fluid samples may be obtained and analyzed using different techniques. If there are no changes in the abundance ratio trends (line 420), abundance ratios from additional measurement stations may be obtained and plotted versus depth to compare with the previously obtained abundance ratios and trends (block 422). As shown in the process 400, the additional trends may be evaluated to determine if there are changes in the trends (decision block 414) that may necessitate investigation into reservoir changes.

Figure 5A:
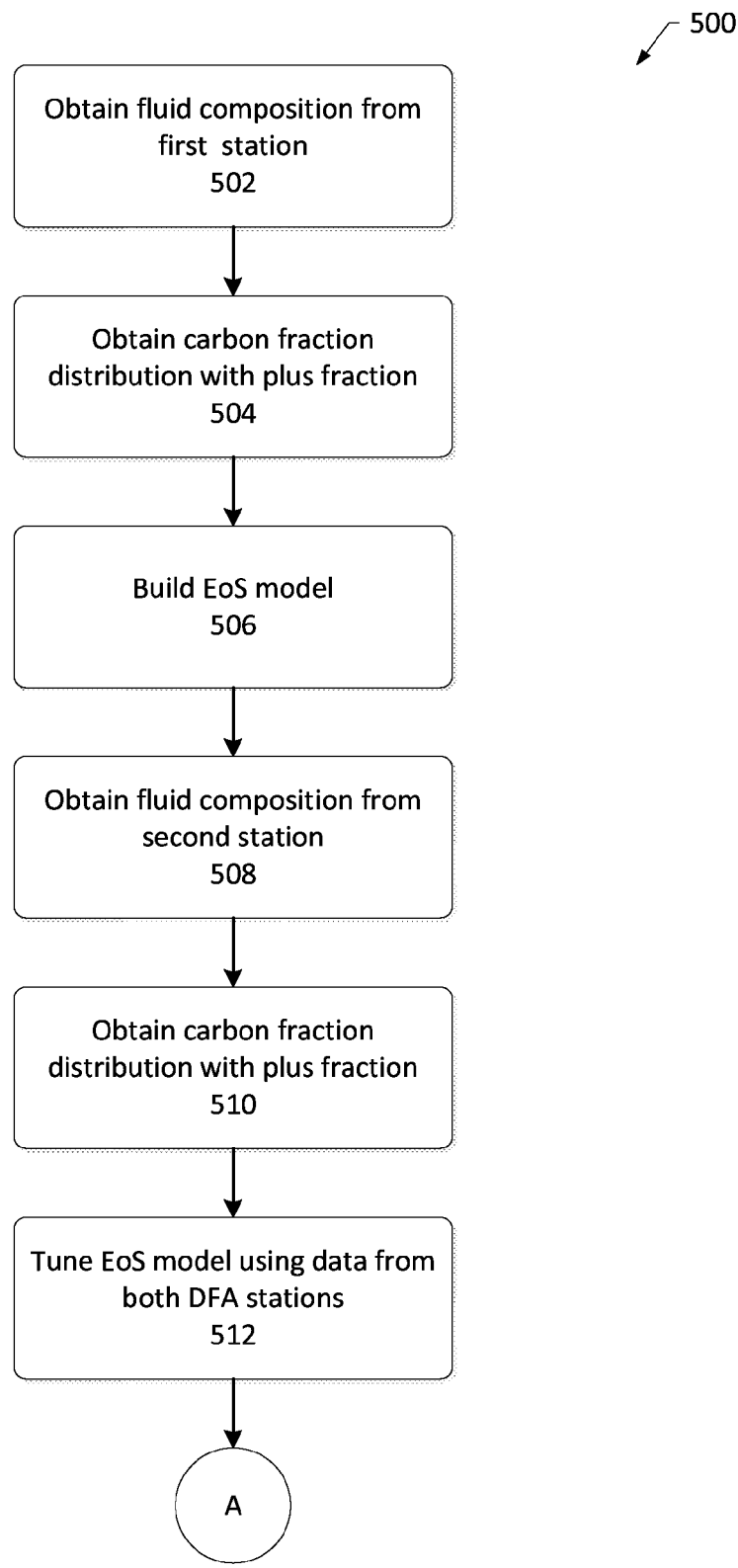
FIGS. 5A and 5B are block diagrams of an example process for reservoir analysis using fluid predictions without offset well information in accordance with an embodiment of the disclosure.
Figure 5B:
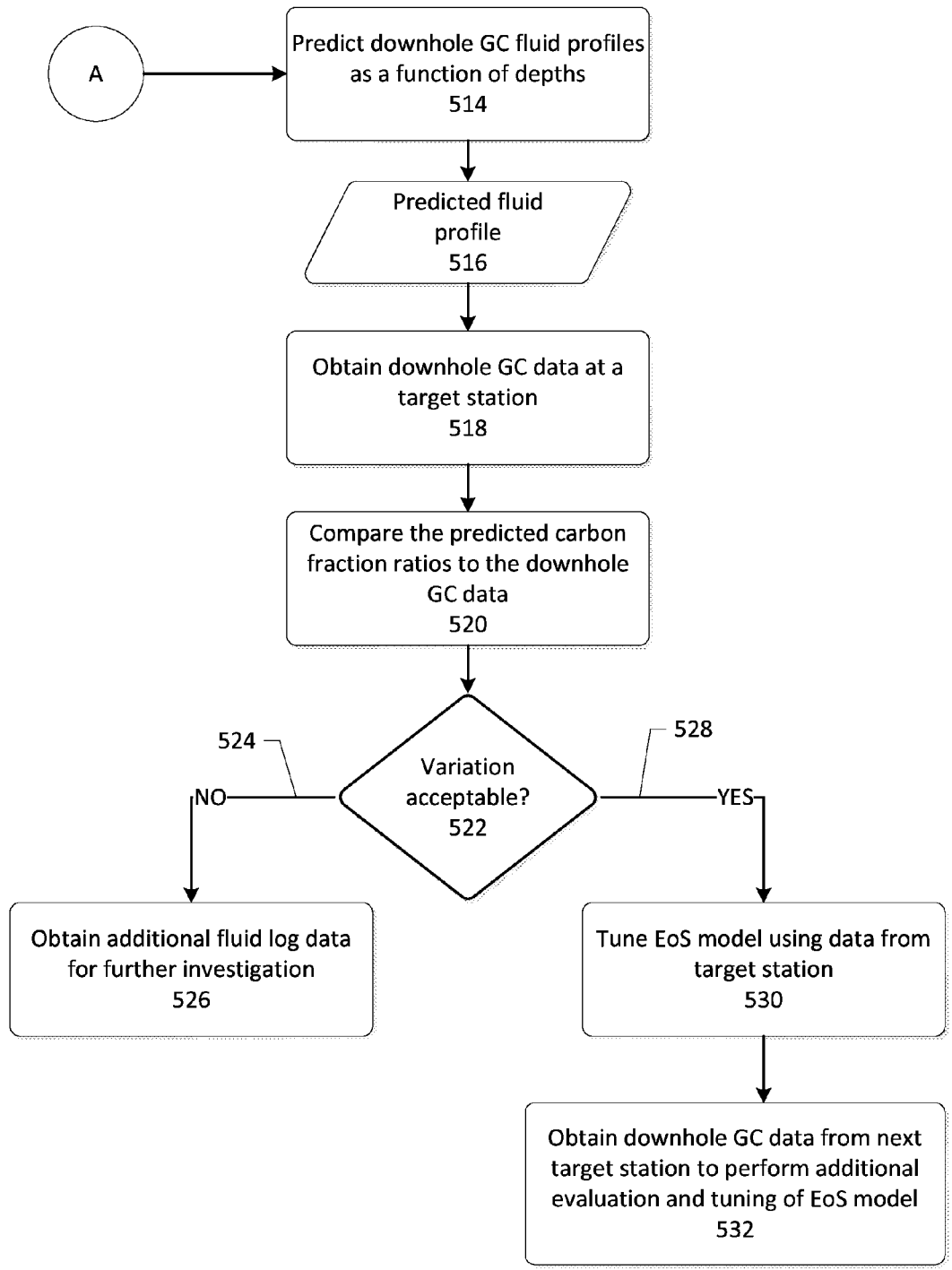

In some embodiments, downhole GC measurements may be used with other measurements, such as measurements obtained via optical analysis, pressure and temperature measurements and so on, to build an Equation of State (EoS) model for a fluid. For example, as noted above, embodiments of the fluid analysis tool 62 may obtain one or more of these measurements using the one or more fluid analysis modules 72. FIGS. 5A and 5B depict a process 500 for reservoir analysis using fluid predictions without offset well information in accordance with an embodiment of the disclosure. Initially, a composition of a fluid may be obtained from a first measurement station having sufficient data to build an EoS model (block 502). As described above, the composition may be determined from measurements of a fluid sample acquired at the first measurement station by using the fluid analysis module 72 of the fluid analysis tool 62 described above. For example, the first station may be a DFA station having both a GC module and an optical analysis module in the fluid analysis tool 62. In such embodiments, the fluid composition may be determined by integrating the GC measurements with the optical measurements. Thus, in some embodiments, a hydrocarbon fraction distribution with a plus fraction may be obtained from the measurements of the first measurement station (block 504). In some embodiments, obtaining measurement data from a station may be referred to as logging the station, e.g., obtaining a fluid log that provides measurements from the fluid analysis tool 62.

Accordingly, an EoS model may be built from the obtained fluid composition and any other data obtained at the first station (block 506). In some embodiments, the fluid composition and EoS model for a low contamination fluid may be obtained after performing a cleanup of the fluid for analysis. For example, after performing a cleanup and obtaining a less contaminated fluid sample, the plus fraction for an obtained gas chromatogram may be estimated using or in combination with other fluid analysis techniques. Next, a second fluid composition from a second station may be obtained from a second measurement station (block 508). The second composition may be determined from measurements of a fluid sample acquired at the second measurement station by using the fluid analysis module 72 of the fluid analysis tool 62 described above. For example, here again the second station may be a DFA station having both a GC module and an optical analysis module in the fluid analysis tool 62. Accordingly, a second hydrocarbon fraction with plus fraction may be obtained using measurements from the second station (block 510). The previously built EoS model may be tuned to match the fluid compositions (and, in some embodiments, other data) obtained from the first and second measurement stations (block 512). Here again, the second fluid composition and tuning of the EoS model for a low contamination fluid may be performed after a cleanup of the heavily contaminated fluid for analysis, such as to enable the determination of a plus fraction to enable quantification of components of the fluid.

As shown by connection block A, FIG. 5B further illustrates operations of the process 500. Using the EoS model built from the obtained fluid compositions, the downhole GC fluid profiles as a function of depths may be predicted (block 514) to generate a predicted fluid profile (block 516). In some embodiments, the predicted fluid profile 516 may include or be referred to as a fluid log. The predicted fluid profile 516 may be generated using the assumption that all stations are contained in the same hydraulic flow unit and that the fluid column is in equilibrium. In some embodiments, a predicted fluid profile may include hydrocarbon fraction ratios up to C9 (e.g., C1 through C8) versus depth.

Next, downhole GC measurements (i.e., a gas chromatogram) from a downhole GC module may be obtained at a target measurement station (block 518). For example, the downhole GC measurements may be obtained from a fluid analysis tool 62 having a GC module (in such embodiments, the fluid analysis tool 62 may only have a GC module and may not have an optical analysis module or other modules). As will be appreciated, the downhole GC measurements may include component ratios such as, for example, hydrocarbon fraction ratios. As mentioned above, in some embodiments the component ratios for a heavily contaminated fluid may be obtained in a relatively short amount of time (e.g., by obtaining components ratios for hydrocarbon fractions below C9 and avoiding a cleanup of the fluid).

The downhole GC measurements may be compared to the predicted fluid profile (block 520) to determine a variation between the predicted fluid profile 516 and the measured downhole GC measurements. The variation may be evaluated to determine whether the variation is acceptable (decision block 520). For example, in some embodiments the variation may be compared to a threshold. In some embodiments, if the variation is greater than the threshold, the variation may be unacceptable. In other embodiments, suitable statistical techniques may be used to determine whether a variation is acceptable or unacceptable. If the variation is not acceptable (line 524), then the equilibrium assumption, the hydraulic flow assumption, or both, may be considered incorrect. In some embodiments, additional fluid log data may be obtained from additional stations for further investigation (block 526). In some embodiments, variations from the predicted fluid profile may be used for additional determinations or investigations, e.g., whether a formation is compartmentalized, whether oil-water contact is being approached, and so on.

If the variation is acceptable (line 528), the vertical connectivity assumption used to generate the predicted fluid profile 516 may be considered correct and the EoS model may be refined using the obtained downhole GC measurements (block 530). In some embodiments, downhole GC measurements may be obtained from next target station and additional evaluation and turning of the EoS model may be performed (block 532). As mentioned above, the additional downhole GC measurements may include component ratios such as, for example, hydrocarbon fraction ratios.

In some embodiments, fluid predictions may be performed using data from offset wells. In such embodiments, the data acquired from offset wells may include sufficient fluid compositional information to build an EoS model. Such data may include, for example, data from laboratory sample analysis, DFA, or both. The EoS model built from offset wells data may be used to predict fluid properties and DFA for a target well that intersects the same compartment. The predicted fluid profile is generated using the assumption that the target well and offset wells are contained in the same hydraulic flow unit and that the fluid column is in equilibrium. Accordingly, FIG. 6 depicts a process 600 for reservoir analysis using fluid predictions with offset well information in accordance with an embodiment of the disclosure. Initially, data from one or more offset wells may be obtained (block 602). In some embodiments, the data may include measurements of fluid samples acquired in an offset well and analyzed in a surface laboratory, measurements obtained using DFA from measurements stations in the offset wells, or any combination thereof. The data may also include fluid composition determined from such measurements. Accordingly, an EoS model for a reservoir fluid may be built using the offset well data (block 604).

Figure 6:
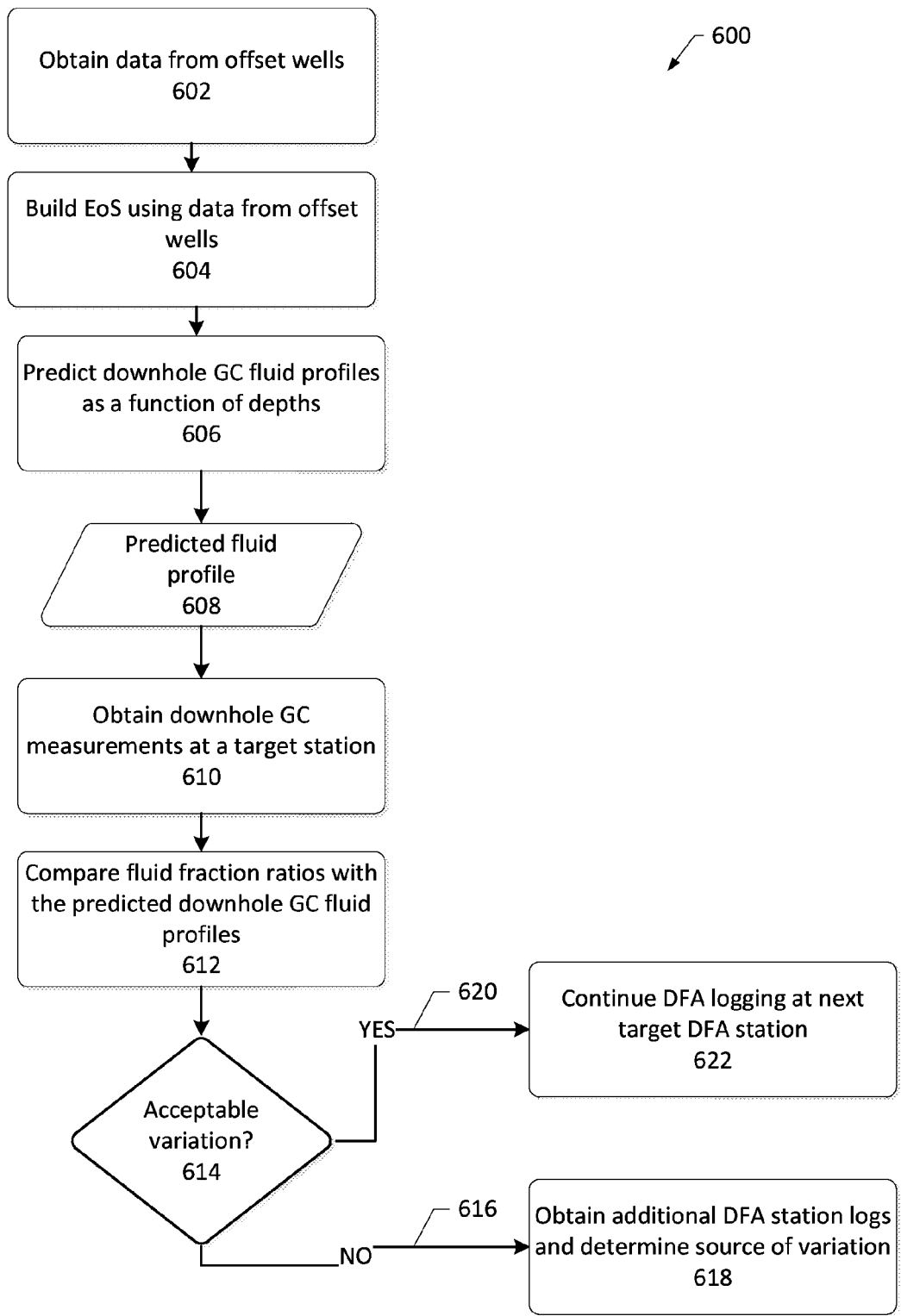
FIG. 6 is a block diagram of an example process for reservoir analysis using fluid predictions using offset well information in accordance with an embodiment of the disclosure.

Next, as shown in FIG. 6, downhole GC fluid profiles as a function of depths may be predicted using the EoS model (block 606) to produce a predicted fluid profile 608. In some embodiments, the predicted fluid profile 608 may include or be referred to as a fluid log. In some embodiments, the predicted fluid profile 608 may include component concentration distribution and peak ratios of hydrocarbon fractions up to C9 (e.g., C1 through C8). Next, downhole GC measurements may be obtained at a target measurement station (block 610). For example, the downhole GC measurements may be obtained from a fluid analysis tool 62 having a GC module (in such embodiments, the fluid analysis tool 62 may only have a GC module and may not have an optical analysis module or other modules). As will be appreciated, the downhole GC measurements may include component ratios such as, for example, hydrocarbon fraction ratios. As mentioned above, in some embodiments the component ratios for a heavily contaminated fluid may be obtained in a relatively short amount of time (e.g., by obtaining components ratios for hydrocarbon fractions below C9 without performing a cleanup of the fluid). The component ratios from the downhole GC measurements may be compared to the predicted fluid profile (block 612) to determine a variation between the predicted fluid profile 608 and the downhole GC measurements.

The variation may be evaluated to determine whether the variation is acceptable (decision block 614). For example, in some embodiments the variation may be compared to a threshold. In some embodiments, if the variation is greater than the threshold, the variation may be unacceptable. In other embodiments, suitable statistical techniques may be used to determine whether a variation is acceptable or unacceptable. If the variation is not acceptable (line 616), then the equilibrium assumption to the one or more offset wells, the hydraulic flow assumption to the one or more offset wells, or both, may be considered incorrect. In some embodiments, additional fluid log data may be obtained from additional stations for further investigation (block 618). In some embodiments, variations from the predicted fluid profile may be used for additional determinations or investigations, e.g., whether a formation is compartmentalized, whether oil-water contact is being approached, and so on.

If the variation is acceptable (line 620), then the assumed fluid equilibrium and flow connectivity (hydraulic flow) to the one or more offset wells may be considered correct. In some embodiments, downhole GC measurements may be obtained from next target station and additional evaluation and turning of the EoS model may be performed (block 622). As mentioned above, the additional downhole GC measurements may include component ratios such as, for example, hydrocarbon fraction ratios. These operations may be performed until the reservoir and fluid are sufficiently characterized.

Conditional language, such as, among others, "can," "could," "might," or "may," unless specifically stated otherwise, or otherwise understood within the context as used, is generally intended to convey that certain implementations could include, while other implementations do not include, certain features, elements, and/or operations. Thus, such conditional language is not generally intended to imply that features, elements, and/or operations are in any way used for one or more implementations or that one or more implementations necessarily include logic for deciding, with or without user input or prompting, whether these features, elements, and/or operations are included or are to be performed in any particular implementation.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense and not for purposes of limitation.

What is claimed is:

1. A method for analyzing a reservoir traversed by a wellbore, comprising:
    obtaining, from a first measurement station within the wellbore, a first at least one abundance ratio from a first gas chromatogram of a first fluid sample acquired at the first measurement station;
    obtaining, from a second measurement station within the wellbore, a second at least one abundance ratio from a second gas chromatogram of a second fluid sample acquired at the second measurement station;
    identifying a trend between the first at least one abundance ratio and the second at least one abundance ratio from the first plot;
    obtaining, from a third measurement station within the wellbore, a third at least one abundance ratio from a third gas chromatogram of a third fluid sample acquired at the third measurement station;
    determining, using the third at least one abundance ratio, whether a change exists in the abundance ratio trend; and
    using the determination to analyze the reservoir.

2. The method of claim 1, wherein identifying the abundance ratio trend between the first at least one abundance ratio and the second at least one abundance ratio from the first plot comprises:
    plotting the first at least one abundance ratio and the second at least one abundance ratio versus depth to produce a first plot; and
    identifying the abundance ratio trend from the first plot.

3. The method of claim 2, wherein determining, using the third at least one abundance ratio, whether a change exists in the abundance ratio trend comprises:
    plotting the first at least one abundance ratio, the second at least one abundance ratio, and the third at least one abundance ratio versus depth to product a second plot; and
    identifying a change in abundance ratio trend from the second plot.

4. The method of claim 1, wherein the first fluid sample is acquired without performing a cleanup of the fluid and the second fluid sample is acquired without performing a cleanup of the fluid.

5. The method of claim 1, wherein the first gas chromatogram comprises a first composition ratio of hydrocarbon fractions C1 through C8.

6. The method of claim 1, wherein the second gas chromatogram comprises a second composition ratio of hydrocarbon fractions C1 through C8.

* * * * *